United States Patent [19]

Peterson, Jr. et al.

[11] 4,276,424

[45] Jun. 30, 1981

[54] METHODS FOR THE PRODUCTION OF ORGANIC POLYSILANES

[75] Inventors: William R. Peterson, Jr., Fallsington; Barry C. Arkles, Oreland, both of Pa.

[73] Assignee: Petrarch Systems, Levittown, Pa.

[21] Appl. No.: 99,266

[22] Filed: Dec. 3, 1979

[51] Int. Cl.³ .............................................. C07F 7/12
[52] U.S. Cl. .................................................... 556/430
[58] Field of Search .......................................... 556/430

[56] References Cited

U.S. PATENT DOCUMENTS

| | | | |
|---|---|---|---|
| 3,146,248 | 8/1964 | Alsgaard et al. | 556/430 |
| 3,146,249 | 8/1964 | Alsgaard et al. | 556/430 |

FOREIGN PATENT DOCUMENTS 143803   4/1961   U.S.S.R. .................................. 556/430

OTHER PUBLICATIONS

West et al., "Inorganic Synthesis", pp. 265-268, (1979).
"Journal of Organometallic Chemistry", 5, pp. 201-202, 1966.

*Primary Examiner*—Paul F. Shaver
*Attorney, Agent, or Firm*—Seidel, Gonda, Goldhammer & Panitch

[57] ABSTRACT

Organic polysilanes may be produced in a simpler, safer and more economic manner by reacting an organohalosilicon hydride with lithium metal or lithium-alkali metal alloy. According to the reaction the silicon-silicon bonds of the organopolysilane are formed by the removal of halogen and hydrogen from the hydride. Particularly important is the formation of dodecamethylcyclohexasilane by the reaction of dimethyl chlorosilane with lithium metal. Simpler polysilanes may be produced by adding to the reaction mixture endcappers such as trifunctional organohalosilanes without an Si-H bond.

10 Claims, No Drawings

METHODS FOR THE PRODUCTION OF ORGANIC POLYSILANES

BACKGROUND OF THE INVENTION

The present invention is directed to the production of organic polysilanes in a safer, simpler and more economic manner than possible by prior art methods. More particularly, the invention is directed to the production of dodecamethylcyclohexasilane and simpler polysilanes.

Organic polysilanes are chemical substances in which there is more than one silicon to silicon bond in the molecule with organic groups also bound to the silicons. The organopolysilanes are of utility as organic intermediates and precursors for high temperature polymers. Dodecamethylcyclohexasilane is of great current interest because it yields reactive silylene when treated with ultraviolet radiation, and because it is a precursor to oriented silicon carbide.

The general method for the production of polysilanes is the treatment of organohalosilanes with an alkali metal, usually sodium, under pressure. The method currently employed for the production of dodecamethylcyclohexasilane involves the reaction of sodium-potassium alloy on dimethyldichlorosilane to yield a complex mixture of polysilanes. The polysilanes are then reequilibrated to the cyclic hexamer. This synthesis is described by R. West in *Inorganic Synthesis*, page 265 (Wiley 1979).

The synthesis of polysilanes as described above may be represented by the following equation:

$$RR'SiX_2 + 2M \rightarrow (RR'Si)_n + 2MX$$

where R and R' are organic groups selected from alkyl, aryl or equivalent groups, usually lower alkyl, X is halogen, and M is an alkali metal or alkali metal alloy.

The above methods have several disadvantages which make the production of polysilanes difficult, dangerous and/or uneconomic. As noted above the treatment of organohalosilanes with alkali metal requires the use of pressure. Also, sodium-potassium alloy is a pyrophoric metal which is extremely danagerous to handle. These and other disadvantages of the prior art are alleviated by the methods of the present invention.

BRIEF SUMMARY OF THE INVENTION

According to the present invention, a simple, economic and relatively safe method of producing organopolysilanes has been discovered in which organohalosilanes containing a hydrogen bound to the silicon are treated with lithium metal or lithium-alkali metal alloy to form silicon-silicon bonds by the removal of halogen and hydrogen from the organohalosilane. A particularly preferred method of the present invention is the production of dodecamethylcyclohexasilane by reaction of dimethylchlorosilane with lithium metal. However, by the addition of endcappers such as trimethylchlorosilane to the reaction mixture, simpler polysilane may be produced.

DETAILED DESCRIPTION OF PREFERRED EMBODIMENTS

The methods of the present invention may be represented by the following simplified general equation:

$$2RR'SiHX + 2M \rightarrow (RR'Si)_n + 2MX + H_2 \uparrow$$

where R and R' are alkyl, aryl or equivalent groups which are stable in the presence of alkali metal, X is halogen, and M is lithium metal or lithium-alkali metal alloy.

R and R' are usually lower alkyl, especially methyl or ethyl, and may be the same or different. X is preferably chlorine, but may be other halogen, usually bromine. Examples of organohalosilicon hydrides (RR'SiHX) which may be used as starting materials in the present invention include dimethylchlorosilane dimethylbromosilane and methylethylchlorosilane. However, the invention is not intended to be limited to these particular silanes.

The metal with which the organohalosilicon hydrides is treated may be lithium metal or lithium-alkali metal alloys which will react with the halogen and hydrogen to release hydrogen gas and yield the metal halide. Among the lithium-alkali metal alloys which may be used are lithium-sodium alloys, since sodium is nearly always present as a contaminant in lithium.

The reactions of the present invention proceed readily under mild conditions without the necessity of using elevated pressures. As with any reaction involving the use of alkali metals, the reaction must be totally anhydrous and in the absence of reactive oxygen. The reaction may be carried out in any suitable solvent or vehicle which does not adversely affect the reactants or products, and tetrahydrofuran is particularly suitable.

There is usually a variable induction period for the initiation of the reactions of the present invention. Upon initiation of the reaction, a distinct exotherm is observed along with a mild evolution of hydrogen. The procedures for distilling the vehicle and recovering the organopolysilane product are conventional and will be obvious to those of ordinary skill in the art, particularly with reference to the specific examples set forth below.

The invention will now be described in further detail by reference to the following specific, non-limiting example which illustrates the production of dodecamethylcyclohexasilane:

EXAMPLE I

A 12 liter four neck flask was equipped with a mechanical stirrer, a slow nitrogen purge, a dry-ice/acetone Dewar condenser, and an addition funnel. The flask was thoroughly dried by heating with an infra-red light under the nitrogen purge prior to cooling the condensor. The flask was then charged with 2000 mls of anhydrous tetrahydrofuran. 333.2 g of 50% lithium metal dispersion in mineral oil was then added. Approximately 500 mls additional tetrahydrofuran was used to aid in transfer of the lithium dispersion.

Stirring was commenced and a 400 ml portion of dimethylchlorosilane was added slowly over four hours. The addition of a total of 2670 mls of dimethylchlorosilane was made over four days. The mixture was then heated to reflux with two IR lamps while stirring for six hours.

The mixture was allowed to cool, and then decanted from salts and filtered through glass wool in order to remove unreacted lithium. Tetrahydrofuran was then removed by stripping distillation. Temperature of distillate did not exceed 66° C. When stripping was completed, heating was increased until a small amount of material began to distill at 100° C. At this point heating was halted.

On cooling overnight large rhombic crystals formed beneath an oily liquid layer. The liquid layer was decanted. A quantity of warm tetrahydrofuran was added sufficient to redissolve the crystals. The mixture was chilled overnight and crystals reformed. Again the supernatant was discarded and the crystals were packaged in amber glass.

The total yield of product was 812 g. The structure of dodecamethylcyclohexasilane was confirmed by IR, NMR and mass spectra.

The general method of the present invention has a much greater tendency to produce cyclic rather than linear polysilanes. However, much simpler polysilanes may be produced by the addition of endcappers to the reaction mixture. For example, trifunctional organohalosilanes which do not have a silicon-hydrogen bond may be added as endcappers to produce lower molecular weight and linear organopolysilanes. Such trifunctional organohalosilanes may be represented by the general formula RR'R"SiX wherein R" is selected from the same group as R and R', that is alkyl, aryl and equivalent organic groups which are stable in the presence of alkali metal.

The endcapping reactions of the present invention will now be described in more detail by reference to the following specific, non-limiting example which illustrates trimethylsilyl terminated polysilanes:

EXAMPLE II

Under conditions described in Example I, a 5 liter flask was charged with 1200 mls of tetrahydrofuran (THF) and 55.5 g of lithium metal powder washed free of mineral oil by suspension in hexane. A mixture of 760 mls of trimethylchlorosilane and 222 mls of dimethylchlorosilane was introduced dropwise. The reaction proceeded analagously and was worked-up according to Example I.

The filtered mixture was transferred to a single neck 3 liter flask and distilled through a heated one meter glass helix packed column. The following fractions were recovered:

70° C.—mostly THF and traces of unreacted chlorosilanes;
111°–113° C.—hexamethyldisilane 196 g;
174°–176° C.—octamethyltrisilane 245 g.

At this point the mixture was cooled to room temperature and transferred to a 500 ml flask. Distillation was recommennced under 30 mm vacuum.

The following fractions were recovered:
118°–119° C.—decamethyltetrasilane 56 g;
163°–167° C.—dodecamethylpentasilane 17 g.

Gas chromatography analysis of fractions showed a minimum purity of 95%.

The present invention may be embodied in other specific forms without departing from the spirit or essential attributes thereof and, accordingly, reference should be made to the appended claims, rather than to the foregoing specification, as indicating the scope of the invention.

We claim:

1. A method for producing organopolysilanes by reacting an organohalosilicon hydride with lithium metal or lithium-alkali metal alloy, whereby the silicon-silicon bonds of the organopolysilanes are formed by the removal of halogen and hydrogen from the hydride.

2. A method for producing organopolysilanes according to claim 1 wherein the organopolysilane is represented by the formula:

$$(RR'Si)_n$$

the organohalosilicon hydride is represented by the formula:

$$RR'SiHX$$

wherein X is halogen and R and R' are alkyl, aryl or equivalent groups which are stable in the presence of alkali metals.

3. A method according to claim 2 wherein the reaction is represented by the general equation:

$$2RR'SiHX + 2M \rightarrow (RR'Si)_n + 2MX + H_2 \uparrow$$

wherein M is lithium or lithium-alkali metal alloy.

4. A method according to claim 1 wherein the alloy is lithium-sodium alloy.

5. A method according to claim 1 wherein dodecamethylcyclohexasilane is produced by reacting dimethylchlorosilane with lithium metal.

6. A method according to claim 2 wherein R and R' are lower alkyl.

7. A method according to claim 1 wherein the reaction is carried out in the presence of tetrahydrofuran which is subsequently removed by stripping distillation.

8. A method according to claim 1 wherein an organohalosilane without a silcon-hydrogen bond is present in the reaction mixture to terminate the organopolysilane.

9. A method according to claim 2 wherein an organohalosilane of the formula:

$$RR'R"SiX$$

wherein R" is selected from the same group as R and R', is present in the reaction mixture to terminate the organopolysilane.

10. A method according to claim 1 wherein dimethylchlorosilane is reacted with lithium, and trimethylchlorosilane is present in the reaction mixture as an endcapper for the organopolysilanes.

* * * * *